US012590293B2

(12) United States Patent

Gutiérrez Gutiérrez et al.

(10) Patent No.: US 12,590,293 B2
(45) Date of Patent: Mar. 31, 2026

(54) METHOD FOR OBTAINING A PLATELET DERIVED SECRETOME AND USES THEREOF

(71) Applicants: FUNDACIÓN PARA LA INVESTIGACIÓN E INNOVACIÓN BIOSANITARIA DEL PRINCIPADO DE ASTURIAS (FINBA), Oviedo Asturias (ES); UNIVERSIDAD DE OVIEDO, Oviedo Asturias (ES)

(72) Inventors: Laura Gutiérrez Gutiérrez, Oviedo Asturias (ES); Andrea Acebes Huerta, Oviedo Asturias (ES)

(73) Assignees: UNIVERSIDAD DE OVIEDO, Oviedo Asturias (ES); FUNDACIÓN PARA LA INVESTIGACIÓN E INNOVACIÓN BIOSANITARIA DEL PRINCIPADO DE ASTURIAS (FINBA), Oviedo Asturias (ES)

( * ) Notice: Subject to any disclaimer, the term of this patent is extended or adjusted under 35 U.S.C. 154(b) by 0 days.

(21) Appl. No.: 18/294,032

(22) PCT Filed: Aug. 24, 2022

(86) PCT No.: PCT/IB2022/057936
§ 371 (c)(1),
(2) Date: Jan. 31, 2024

(87) PCT Pub. No.: WO2023/026213
PCT Pub. Date: Mar. 2, 2023

(65) Prior Publication Data
US 2024/0263137 A1 Aug. 8, 2024

(30) Foreign Application Priority Data

Aug. 24, 2021 (ES) ............................... ES202130806

(51) Int. Cl.
*C12N 5/078* (2010.01)
*A61K 9/14* (2006.01)
*A61K 35/19* (2015.01)
*C12M 1/00* (2006.01)

(52) U.S. Cl.
CPC .............. *C12N 5/0644* (2013.01); *A61K 9/14* (2013.01); *A61K 35/19* (2013.01); *C12M 47/06* (2013.01)

(58) Field of Classification Search
CPC ........ C12N 5/0644; A61K 9/14; A61K 35/19; C12M 47/06
See application file for complete search history.

(56) References Cited

U.S. PATENT DOCUMENTS

| | | | |
|---|---|---|---|
| 5,599,558 A | 2/1997 | Gordinier | |
| 2019/0321408 A1* | 10/2019 | Gooris | ................... A61K 38/18 |
| 2022/0008475 A1* | 1/2022 | Feys | ...................... A61K 33/14 |

OTHER PUBLICATIONS

Scully et al. "Optimising platelet secretomes to deliver robust tissue-specific regeneration." Journal of Tissue Engineering and Regenerative Medicine 14.1 (2020): 82-98. (Year: 2020).*
Burzynski et al. "Platelet isolation and activation assays." Bio-protocol 9.20 (2019): e3405-e3405. (Year: 2019).*
Vinholt et al. "Light transmission aggregometry using pre-coated microtiter plates and a Victor X5 plate reader." PLoS One 12.10 (2017): e0185675. (Year: 2017).*
Bonferoni et al. "Bioactive medications for the delivery of platelet derivatives to skin wounds." Current Drug Delivery 16.5 (2019): 472-483. (Year: 2019).*
International Search Report and Written Opinion, issued for the corresponding International Application No. PCT/IB2022/057936, mailed Nov. 29, 2022, 6 pages.
Scully, David et al., "Platelet releasate promotes skeletal myogenesis by increasing muscle stem cell commitment to differentiation and accelerates muscle regeneration following acute injury", Acta Physiologica, Nov. 14, 2018, GB vol. 225, No. 3.
Scully, David et al., "Optimising platelet secretomes to deliver robust tissue-specific regeneration", Journal of Tissue Engineering and Regenerative Medicine, Nov. 11, 2019, US vol. 14, No. 1, pp. 82-98.
Maguire, Patricia B. et al., "Comparative Platelet Releasate Proteomic Profiling of Acute Coronary Syndrome versus Stable Coronary Artery Disease", Frontiers in Cardiovascular Medicine, Jan. 1, 2020, vol. 7, Article 101.
Gianazza, Erica et al., "Platelets in Healthy and Disease States: From Biomarkers Discovery to Drug Targets Identification by Proteomics", International Journal of Molecular Sciences, Jun. 25, 2020, vol. 21, No. 12, p. 4541.
International Preliminary Report on Patentability, issued for the corresponding International Application No. PCT/IB2022/057936, mailed Nov. 29, 2023, 8 pages.

* cited by examiner

*Primary Examiner* — Emily A Cordas
(74) *Attorney, Agent, or Firm* — LUCAS & MERCANTI, LLP

(57) ABSTRACT

A method for obtaining secretomes from platelets and the secretome uses in regenerative medicine, in the treatment of diseases, including cell therapy, and in vitro cell culture. This method is developed with the aim of obtaining platelet-derived bio-products enriched in platelet granular cargo, rich in growth factors, and depleted of other platelet-derived molecules and plasma for universal use. The method avoids the use of platelet inhibitors or temperature-shock during the process, assuring the integrity of the platelet biological source. Furthermore, the potential processing of the product would allow additional clinical applications and solve storage limitations. This method and the characterization thereof of secretomes at the molecular level in health and disease will contribute to the identification of biomarkers for disease diagnosis and prognosis.

7 Claims, 7 Drawing Sheets

α-granules

AGGA
COL-30
COL-90
CVX
PMA
TRAP6
Unstimulated $10^0$  $10^1$  $10^2$

CD62P

δ-granules and lysosomes

AGGA
COL-30
COL-90
CVX
PMA
TRAP6
Unstimulated $10^0$  $10^1$  $10^2$  $10^3$  $10^4$

CD63

| Bioproduct | Platelet count (PLTs/µl) |
|---|---|
| Platelet-Rich Plasma (PRP) | Range 262-728 x 10³ |
| | Mean 487.9±241 x 10³ |
| Platelet Secretome (PLT-S) | 200 x 10³ |

METHOD FOR OBTAINING A PLATELET DERIVED SECRETOME AND USES THEREOF

CROSS-REFERENCE TO RELATED APPLICATIONS

This application is a 371 of PCT/IB2022/057936, filed Aug. 24, 2022, which claims the benefit of Spanish Patent Application No. P202130806, filed Aug. 24, 2021, each of which are incorporated herein by reference.

The present invention relates to a unique method for obtaining platelet secretomes, its characterization and distinctive properties for its uses thereof in regenerative medicine (with therapeutic or aesthetic endpoint), in the treatment and potential diagnosis of diseases, and in in vitro cell culture, including cell therapy. Therefore, the present invention belongs to the fields of medicine, medical compositions and diagnosis of diseases.

BACKGROUND ART

Platelets are the anucleated blood components that are responsible for maintaining the body hemostasis. In recent years, new functions have been attributed to platelets showing that they are involved in many other physiological and pathological processes beyond hemostasis, such as immunomodulation, lymph and blood vessel separation during development, angiogenesis and tumor metastasis. In physiological conditions, the exposure of collagen and release of von Willebrand factor following an endothelial damage is recognized by platelets that become activated and adhere at the site of injury. This activation induces signaling pathways that lead to shape conformational changes and integrin activation favoring platelet aggregation and release of their granular cargo. The platelet secretome (also called platelet releasate) contains a multitude of growth factors, chemokines, cytokines, and inflammatory mediators, including platelet-derived growth factor (PDGF), epidermal growth factor (EGF), transforming growth factor-beta 1 (TGF-β1), vascular endothelial growth factor (VEGF) and basic fibroblast growth factor (FGF) to name but a few, that participate in the key stages of wound healing and tissue regenerative processes, including cell migration, differentiation, proliferation and neovascularization.

The role of platelets in tissue regeneration and wound healing and the knowledge that they are a natural reservoir of growth factors has resulted in the development of platelet-based bio-products, such as Platelet Rich Plasma (PRP) or Platelet Lysates (PL), as adjuvant therapy in regenerative medicine. The therapeutic use of platelet-based bio-products constitutes a relatively new approach in regenerative medicine with clinical benefits in a wide range of medical fields, such as dental and maxillofacial surgery, ophthalmology, sports medicine, veterinary and aesthetic medicine, among others. However, the literature in the field reflects the lack of consensus of preparation methods, and lack of consensus in the description of the product used in the daily clinical practice (at the cellular and molecular level). PRP is defined as the plasma fraction that results after differential centrifugation of blood and contains a supraphysiological concentration of platelets. PRP might be applied fresh (thus containing living platelets), or after activation or freezing/thawing (to allow the release of platelet cargo), without making nomenclature distinctions in the literature. On the other hand, PL refer to products where platelets have been lysed by using different methodologies (mechanical, chemical). However, often there is no specification as to whether the primary material contains or not plasma before inducing platelet lysis. Furthermore, the use of PRPs/PLs is indicated generally for autologous use, and while research is conducted for validating the potential application of either homologous or heterologous (allogenic) platelet-derived bio-products, there is increasing demand for producing a universal product (that provides both donor-independency and safety).

The therapeutic outcome of platelet-based therapies remains highly controversial due to the above-mentioned lack of consensus on PRP or PL preparation, processing, storage and application methods which results in a highly variable composition of PRP in terms of platelet number, presence or not of white blood cells and subsequent growth factor concentration and activity of bio-active molecules, which also lacks characterization. Furthermore, PRP and PLs contain a mixture of plasma and platelet proteins besides the actual bio-active molecules (i.e., those contained in platelet granules), which represent a sub-fraction of the product. In addition, it has also been reported that certain pathological conditions might influence platelet quality and reactivity, and the use of autologous products might not always be the most suitable therapeutic source and may result in uncertainty of expected results due to the subjacent pathology. Thus, there is an increasing clinical demand for the development of novel platelet-derived products that could be used universally and would be more specific or targeted to the pathology being treated in an effort to improve the clinical benefit of the therapy.

In order to generate a platelet-derived bioproduct which is enriched on active bio-molecules, the rationale would indicate to isolate and wash platelets from plasma and to resuspend them in an optimal concentration in an osmotic-solution. Activation of platelets with platelet-receptor agonists will trigger their active degranulation, leaving in the supernatant fraction the platelet secretome, enriched in platelet granule cargo molecules.

Recent works have used such approach to obtain platelet secretomes with different purposes. The US patent document U.S. Pat. No. 5,599,558 discloses a method to study the platelet secretome capacity in vitro, without specifying the methodology (except for mentioning they use the secretome obtained from 109 platelets in 1 mL). Likewise, the document WO2018091713 describes a method to prepare growth factors compositions containing the platelet secretome and the use of such compositions in regenerative medicine.

Despite the existence of documents disclosing methods for the production of platelet derived bio-products, such as PLs described in the documents WO2013113024, EP2389942, EP2757879, or as growth factor solutions obtained from whole blood described in the document U.S. Pat. No. 8,734,854, these are distinct from the product obtained with the current method.

Therefore, there is a need for alternative methods for obtaining platelet releasates exclusively coming from the activation of platelets, free of plasma and other platelet components.

SUMMARY OF THE INVENTION

The invention describes a unique methodology to obtain platelet derived secretomes resulting from the activation of platelets with specific agonists. The inventors notice that the composition of platelet secretomes can be altered due to the activation of platelets, not through contact with platelet agonists, but by change in the physical properties of the platelets during the process of obtaining the platelet secretome. Therefore, the inventors developed a method, herein disclosed, to obtain platelet derived secretome wherein the platelet rich sample is only activated by the action of the platelet agonists and not by change in the physical properties of the platelets during the process of obtaining the secretome. Furthermore, the inventors discovered that the secretome composition depends on the platelet agonist used to induce platelet degranulation.

METHOD OF THE INVENTION

A first aspect of the present invention is an in vitro method for the production of a platelet derived secretome, from here onwards the method of the invention, comprising the following steps:

a) obtaining a non-activated platelet suspension by isolating and resuspending in buffer the platelets from a biological source comprising platelets or platelet rich sample;

b) inducing platelet degranulation by incubating in constant shaking the platelet suspension obtained in step a) with a platelet agonist obtaining a platelet and platelet secretome suspension; and c) collecting the platelet derived secretome by centrifuging the platelet and platelet secretome suspension obtained in step b) to eliminate platelets and other cellular debris, wherein step b) is performed at 35° C. to 40° C. and all other steps are performed at room temperature.

The expression "platelet derived secretome" as used herein refers to the granular content of platelets which is secreted, a process also called "degranulation", when said platelets are activated by activation agents, referred to as "agonists". The term "platelets" as used herein refers to blood platelets. Platelets can be described as the disc-shaped cellular elements in the blood that assist in blood clotting and occur in vertebrate blood.

The first step of the method of the invention comprises the obtention of a non-activated platelet suspension. As such, the expression "obtaining a non-activated platelet suspension by isolating and resuspending in buffer the platelets from a biological source comprising platelets or platelet rich sample" of step a) of the method of the invention refers to the process of separation of the constituent parts of a biological source comprising platelets or platelet rich sample through centrifugation and/or filtration, leading to the formation of fractions, one of such fractions comprising mostly platelets, therefore isolating the platelet fraction which is then resuspended in an appropriate buffer to carry out the remaining steps of the method of the invention. Step a) of the method of the invention allows the removal of non-desired soluble constituents and/or contaminants, obtaining a platelet fraction comprised preferably by at least 95%, 96%, 97%, 98%, 99% or 100% of non-activated platelets. Therefore, in a preferred embodiment the isolating process of step a) of the method of the invention is accomplished by centrifugation and/or filtration. In a more preferred embodiment, the centrifugation is carried out between 3500 and 4500 rpm during 3 to 10 minutes. In a further preferred embodiment, the centrifugation is carried out at 4000 rpm for 5 minutes. In another preferred embodiment the isolating process of step a) of the method of the invention is carried out by filtration with leukocyte depletion filters. The expression "leukocyte depletion filters" as used herein refers to composite filters in which synthetic microfiber material is prepared as a nonwoven web. The filter material may be surface modified to alter surface tension or charge to improve performance in the removal of leukocytes from blood.

Once isolated, the platelets are resuspended in an appropriate buffer. Such buffers are widely known in the field of the invention and the expert in the field would be aware of such buffers and how to use them. In a preferred embodiment the resuspending process of steps a) of the method of the invention is carried out with a buffer selected from a list consisting of: phosphate-buffered saline (PBS), Hanks' Balanced Salt solution (HBSS), HEPES Glucose Buffer, HEPES-buffered Tyrode's. In a further preferred embodiment, the platelet fraction is resuspended to a concentration of 100 to $500\times10^6$ platelets per mL. In a further preferred embodiment, the platelet fraction is resuspended to a concentration of $200\times10^6$ platelets per mL.

The term "platelet rich sample" as used herein refers to samples which contain supraphysiological concentrations of platelets in a carrier, such as plasma or a buffer. Examples of platelet rich samples are platelet rich plasma, platelet concentrate, isolated platelets and ex vivo produced platelets. In a preferred embodiment of the method of the invention the platelet rich sample is selected form a list consisting of: platelet rich plasma (PRP), platelets concentrate, isolated platelets and ex vivo produced platelets.

The term "biological source comprising platelets" refers to part, fraction, portion, or sub-volume considered to be representative of a larger volume of anticoagulated whole blood. In a preferred embodiment of the method of the invention, the biological source comprising platelets is anticoagulated whole blood. The expression "anticoagulated whole blood" as used herein refers to blood itself, collected from a living body with heparin, ethylenediaminetetraacetic acid (EDTA), or any other substance that prevents coagulation, wherein said blood has not been separated into its constituent parts or components, such as serum and plasma. Anticoagulated whole blood can be obtained by venous or arterial phlebotomy in anticoagulated collection tubes, complete or interrupted blood donations from healthy donors, cord blood samples, or other tissues or samples where platelets can be isolated from, such as bone marrow. In preferred embodiment, the anticoagulated whole blood is venous blood, arterial blood, or cord blood. In another preferred embodiment, the whole blood is from an animal, preferably a mammal, more preferably a human of any gender and age.

The term "sample" as used herein refers to part, fraction, portion, or sub-volume considered to be representative of a larger volume of the material/object/volume to be sampled.

The terms "Platelet Rich Plasma" or "PRP" as used herein refer to a supraphysiological concentration of platelets in plasma. For example, the platelet concentration may be 5 times, 10 times, 100 times or more the normal concentration in blood. In addition to platelets, the PRP may comprise traces of other blood components. The non-platelet components, in addition to the plasma, may be white blood cells, erythrocytes and/or any other component present in the blood of the donor. The term "plasma" as used herein refers to the liquid portion of blood where the cellular components are suspended. The plasma makes up about 55% of the whole blood and contains proteins such as albumins, globulins and fibrinogen, water, ions and nutrients.

The term "platelet concentrates" as used herein is intended to encompass the transfusion product comprising platelets, either from pooled whole blood donations or plateletpheresis.

The term "isolated platelets" as used herein refers to platelets that have been isolated from their natural biological carrier (e.g., plasma) and are contained in an artificial carrier (e.g., buffer).

The term "ex vivo produced platelets" as used herein refers to platelets generated from various stem origins, including hematopoietic stem cells, embryonic stem cells and induced pluripotent stem cells or any other stem cell culture which is suitable to be induced to differentiate into platelet cells. Examples and methods of how to produce platelets ex vivo are available in the literature (Buduo, C. A. et al., 2016, Thrombosis and Haemostasis, 115 (02), 250-256; Di Buduo C. A., Blood 2015, 125:2254-2264; Nakagawa Y. et al., Exp Haematol 2013; 41:742-748; Schlinker A. et al., Biotechnol Bioeng 2015; 112:788-800).

As presently described, the platelet rich sample can be obtained from both biological sources such as animals, as well as from in vitro/ex vivo sources, such as cell cultures, specifically stem or induced pluripotent stem (IPS) cell cultures. In accordance, in a preferred embodiment of the method of the invention the platelet rich sample is from an animal, preferably a mammal, more preferably a human being from any age, gender or race. In another preferred embodiment of the method of the invention, the platelet rich sample is from a cell culture, preferably stem cell culture, more preferably hematopoietic stem cell, embryonic stem cell and iPS cell culture.

As stated, one of the possible platelet rich samples is PRP which, in its most common form, is obtained from whole blood. As such, in a preferred embodiment, the method of the invention further comprises an optional step of obtaining a platelet rich sample from a biological source comprising platelets by differential centrifugation without forced deceleration, wherein the optional step is performed before step a). The expression "obtaining a platelet rich sample from a biological source comprising platelets by differential centrifugation without forced deceleration" refers to the process of separating or concentrating the platelets contained in a biological source. To obtain the PRP from an anticoagulated blood sample, the constituent parts of the blood sample must be separated. Such separation is made "by differential centrifugation without forced deceleration". The centrifugation of the anticoagulated blood sample, also called blood fractionation, will apply physical forces to the sample which will lead to the constituent parts of the blood to sediment at different rates depending on their density and mass, forming distinct layers or fractions, which have different compositions. One such fraction is the PRP fraction which can be collected and retained for further processing. In a preferred embodiment the centrifugation is carried out between 100 and 500 g-force during 10 to 20 minutes. In a further preferred embodiment, the centrifugation is carried out at 193 g-force for 15 minutes. Upon finishing the active centrifugation, the sample must come to a stop. The expression "without forced deceleration" as used herein refers to the process of slowing down the centrifuged sample until it comes to a full stop using nothing but the effects of gravity and friction forces inside the centrifuge and its mechanism. Such process is important for the method of the invention, as the inventors found that forced deceleration can lead to platelet activation. Furthermore, the method of the invention does not contemplate the use of inhibitors of platelet aggregation such as apyrase and prostaglandin E2 (PGE2).

As described herein the platelet rich sample can be obtained from different source materials, such as whole blood from where PRP or platelet concentrates are obtained or in vitro culture of platelet cell precursors. Said source materials can be previously treated with pathogen reduction technology to reduce or eliminate disease-causing agents that can be present in said source materials. In a preferred embodiment of the method of the invention, the platelet rich sample is obtained from a sample treated with pathogen reduction technology. The term "pathogen reduction technology" as used herein refers to the method of reducing/eliminating possible disease-causing pathogens by adding riboflavin to the sample source material and irradiating the riboflavin plus the source material with ultraviolet light.

Once obtained, the non-activated platelet suspension must be stimulated or activated to release the content of the granules into the suspension buffer. The expression "inducing platelet degranulation by incubating in constant shaking the platelet suspension obtained in step a) with a platelet agonist obtaining a platelet and platelet secretome suspension" of step b) of the method of the invention refers to such stimulation or activation, whereby the contact of a platelet activator agent or agonist with the platelets leads to the release by the platelets of their granule content into the suspension, a process also called degranulation, originating the "platelet and platelet secretome suspension", an expression which as used herein refers to a suspension comprising both platelets as well as the content of the platelets granules, the platelet secretome, dispersed in the suspension medium. To guarantee a uniform and strong activation of all platelets in the solution, the activation is performed at constant shaking or mixing motion on a device that allows temperature control and mixing of liquid or samples. In a preferred embodiment step b) of the method of the invention is carried out under constant shaking of 500 to 1500 rpm (mixing speed or rotation) for 3 to 10 minutes at 35 to 40 degrees Celsius (° C.), preferably constant shaking of 1000 rpm for 5 minutes at 37° C.

The terms "platelet activating agent" and "platelet agonist" as used herein refer to a compound which is capable of activating platelets thereby initiating the platelet release reaction or degranulation as well as their aggregation. In a preferred embodiment of the method of the invention, the platelet activating agent used in step b) is selected from a list consisting of: Thrombin receptor activator peptide 6 (TRAP6), convulxin, collagen, phorbol myristate acetate (PMA), aggretin A, Adenosine diphosphate (ADP), epinephrin arachidonic acid and thrombin.

In a further embodiment of the method of the invention, the platelet activating agent is conjugated to a label. Such label can be used to posteriorly extract the activating agent from the secretome or detect the activating agent in the secretome.

The term "label" as used herein refers to molecules that can generate a signal that is detectable by a method suitable for such detection. Label detection methods include, but are not limited to, fluorescence, light, confocal and electron microscopy, magnetic resonance and spectroscopy, fluoroscopy, computed tomography and positron emission tomography, enzyme-linked immunosorbent assays, fluorescence detection size exclusion chromatography, lateral flow assay, radioimmunoassay, radio-labelling, western blotting, immunohistochemistry, immunofluorescence, immunocytochemistry, flow cytometry, fluorescence-activated cell sorting, immunoprecipitation and enzyme-type immunospots. Suitable labels include, but are not limited to, fluorescein, rhodamine, eosin and other fluorophores, radioisotopes, gold, gadolinium and other lanthanides, paramagnetic iron, fluorine-18 and other positron-emitting radionuclides or hexa-histidine-tag peptide. In addition, the labels may be bi or multi-functional and detectable by more than one of the methods listed. The label may be, for example, a chromogenic, fluorogenic, magnetic, electrodense, radioactive and/or chemiluminescent compound. In a preferred embodiment of the method of the invention the label is selected from the list consisting of: fluorescein isothiocyanate (FITC), allophocyanine (APC) or any other fluorescent dye relevant in flow cytometry, hexa-histidine-tag peptide, biotin, horseradish peroxidase (HRP), gold beads and paramagnetic iron.

Such labels are conjugated or bound to the activating agent as to form a stable and functional union. Such "conjugation" or "bounding" can be performed by any method known in the art to functionally connect the domains of the activating agent to a label which produces a signal capable of being detected by any one or more of the techniques mentioned in the previous paragraph, such methods to connect domains including without limitation, recombinant fusion with or without intermediate domains, protein-mediated fusion, non-covalent association and covalent bonding, for example, antibody-disulfide bonding, hydrogen bonding, electrostatic bonding and conformational bonding, for example, biotin-avidin associations. Conjugation with a label can occur by chemical or recombinant means. Chemical means refer to a reaction between the activating agent and the label in such a way that a covalent bond is formed between the two molecules to form a single molecule.

In a further embodiment of the method of the invention, the platelet activating agent is attached to a surface. The term "surface" as used herein refers to any surface, material or compound to which the platelet activating agent can be attached to and which does not interfere in any way with the activating function of the agent or with the platelets themselves. Examples of said surfaces include, without limiting to, affinity columns, nanoparticles and lipid components covalent decorated with the activating agent.

As used in the present description, the term "affinity column" refers to a molecular fractionation device comprising beads with specialized chemistry for separating or reacting with biomolecules. The affinity columns to which the present invention refers to, allow for the platelet agonist to be conjugated to the beads as to activate the platelets as they flow through the column.

The term "nanoparticle", as used herein, refers to a particle having a nanoscale dimension and does not express any particular shape constraint. In particular, the term "nanoparticle" includes nanospheres, nanotubes, nanoboxes, nanoclusters, nanorods, and the like. In some embodiments, nanoparticles and/or nuclei of nanoparticles provided in accordance with the present invention generally have a polyhedral or spherical geometry. Having the platelet activating agent conjugated to a surface allows the activation of the platelets as well as facilitating the removal of the agent from the suspension which contains both the platelets and the platelet derived secretome.

Examples of lipid components are 1,2-Distearoyl-sn-glycero-3-phosphocholine (DSPC), 1,2-Distearoyl-sn-glycero-3-phosphoethanolamine-N-[methoxy(polyethylene glycol)-(DSPE-mPEG1000), 1,2-Distearoyl-sn-glycero-3-phosphoethanolamine-N-[maleimide(polyethylene glycol)-2000] (DSPE-PEG2000-Mal) and 1,2-distearoyl-sn-glycero-3-phosphoethanolamine-N-[azido(polyethylene glycol)-2000] (DSPE-PEG2000-Azide), among others.

Once the platelets degranulate, the platelet derived secretome is obtained by separating it from other components present in the solution. Step c) of the method of the invention, "collecting the platelet derived secretome by centrifuging the platelet and platelet secretome suspension obtained in step b) to eliminate platelets and other cellular debris", refers to the process of clearing the medium now rich in components of the platelet granules from cell debris or platelet aggregates trough centrifugation, isolating the platelet secretome. In a preferred embodiment, the centrifugation in step d) of the method of the invention is carried out between 8000 to 13000 g-force during 1 to 10 minutes. In a more preferred embodiment, the centrifugation is carried out at 10000 g-force for 2 minutes. Once centrifuged, the supernatant is transferred to a container.

To guarantee that the platelet derived secretome composition obtained in the step c) of the method of the invention is not altered by external physical factors, all steps of the method of the invention are performed at room temperature, except for step b) of the method of the invention. In addition, no mechanism, process, or technique is employed to stop the activation of the platelets performed in step b) of the method of the invention before performing step c) of the method of the invention. Non limiting examples of such mechanisms, processes or techniques are low temperature shock, e.g., placing the sample on ice, or chemical shock, e.g., treatment with aspirin or prostaglandin E2.

The platelet derived secretome obtained can be freshly used, i.e. used after being obtained, or stored for later use. Depending on the planned use of the platelet derived secretome obtained by the method of the invention, sterilization procedures may be applied. In a preferred embodiment, the method of the invention comprises an optional step comprising the filtering and/or nanofiltering of the platelet derived secretome obtained in step c). Different grades of filtering procedures can be applied. Filtering procedures are performed to filter-sterilize the platelet derived secretome, in order to remove any non-desired bacterial and/or viral contaminant before storage. In a preferred embodiment the filtering is done with a 0.22 microns filter. The term "nanofiltering" as used herein refers to process of filtering with membranes with nanometer sized pores which can remove viral contamination.

Several methods of storage are known in the art that can be applied to the platelet derived secretomes obtained; examples include, without any limitation, freezing, lyophilization, freeze drying, dehydration, encapsulation and nanoencapsulation. Such methods allow the storage of the obtained product in easy-to-use volumes which are easy to reconstitute, as well as providing the platelet derived secretomes with increased stability and accessibility to tissues and/or organs. Therefore, in a preferred embodiment of the method of the invention, the platelet derived secretome obtained in step c) is stored by freezing, lyophilization, freeze drying, dehydration, encapsulation or nanoencapsulation.

Platelet Derived Secretome and its Uses

The present invention discloses a unique method for obtaining platelet derived secretomes whose constituents are dependent only on signaling pathways which are activated by the platelet activating agent or agents and the biological source of the platelets.

Therefore, another aspect of the present invention is a platelet derived secretome, from here onwards the secretome of the invention, obtained by the method of the invention.

The term "platelet derived secretome" has been previously defined regarding the method of the invention and such definition is valid for the current aspects and their embodiments.

The secretome of the invention contains, in relation to an alternative method of the state of the art (i.e. PRP, such as the one obtained using a closed-system as described in Ojea-Pérez A. M. et al, 2019, Transfus Apher Sci., 58 (5), 701-704), an increased cumulative concentration of growth factors, cytokines, chemokines, inflammatory mediators, immunological modulators, as well as a smaller content of factors related with cellular apoptosis/necrosis, after nor-malization considering the number of platelets in the source material. Methods for determining the composition of the platelet derived secretome of the invention and the param-eters to apply such methods are well known by the experts in the field. Such methods include, without limitation, mul-tiplex immunoassays, mass spectrometry assays, chroma-tography, enzyme-linked immunosorbent assay (ELISA), flow cytometry. The expression "determining the composi-tion" as used herein refers to the detection of the presence of a molecule or substance and/or quantification of such mol-ecule or substance in the secretome of the invention.

The term "growth factor" as used herein refers to proteins which stimulate proliferation, survival and/or migration of cells by binding to a specific receptor. Usually, growth factors only act on specific cell types which express the respective receptor. Examples of growth factors and other biomolecules, metabolites and/or biomaterials that can be present in the secretome of the invention include, without limitation, PDGF, PDAF, VEGF, PDGF, PF-4, TGF-B, FGF-A, FGF-B, TGF-A, IGF-1, IGF-2, BTG, TSP, vWF, PAI-1, IgG, IgM, IgA, KGF, EGF, FGF, TNF, IL-1, KGF-2, fibro-peptide A, fibrinogen, albumin, osteonectin, gro-alpha, vit-ronectin, fibrin D-dimer, factor V, antithrombin III, a2 mac-roglobulin, angiogenim, Fg-D, and elastase. In further detail, growth factors, cytokines, or the like that can be present and include, without limitation, LIF, anticancer growth factors such as IGFBP3, eicosanoids such as PGs orleukotrienes, IL-1 TNF alpha, INFs, TNF-α, IL-6, IL-1 (a/b), prostanoid metabolites, complement components, reactive oxygen intermediates, arachidonic acid metabolites, coagulation factors, nitrates, and chemokines. Human derived growth factors, chemokines, cytokines, and hormones can include alpha defensin, alpha synuclein, beta synuclein, 4-1 BBL, 6Ckine, acidic FGF, activin A, avtivin Rib, angiopoietin 2, B-DNF, BAFF, BCA-1, BCA-1, BD-1, BMP-2, BMP-4, BMP-7, BMPRAI, BDNF, CNTF, CTGF, CTI_A-4Fc, CXCL1, CXCL2, cardiotrophin-1, Cripto, Cystatin C, Dkk-1, EGF AOF, EGF, EMAP II, ENA-78, EPO, Eotaxin, FGF basic AOF, FGF-10, FGF-16, FGF 17, FGF 18, FGF19, FGF4, FGF6, FGF7, FGF8, FGF8b, FGF9, Flt3, G-CSF, GDNF, GMCSF, HGF, HGH, IFN alpha A, IFN alpha A D, IFN alpha D, IFN alpha a2b, IFN, beta 1A, IFN-gamma, IGF1, IGFil, IGFBP-4, IGFBP6, ILI alpha, IL-IBeta, IL10, IL11, IL12, IL13, IL15, IL17, IL17A. IL17F, IL18, IL19, IL2, IL20, IL21, IL23, IL28A, IL28B, IL29, IL3, IL31, IL33, IL4, IL5, IL6, IL7, IL8, IL9, IL10, ITAC, KGF2, Kallikreinl 1, Kallikrein4, Kallikrein7, LEFTY-A, LIF, Lep-tin, MCSF AOF, MCSF, MCP-1, MCP2, MCP3, MCP4, MDC, MIG, MIP1 alpha, MIP1 beta, MIP3 alpha, MIP3 beta, MIP4, MIP5, midkine, NAP2, NT3, NT4, Neurotactin, neurturin, Oncostatin, osteoprotegrerin, PDGF-AA, PDGF-AB, PDGF-BB, PTN, Rank ligand, Rank receptor, RANTES<SCF, SCFAOF, SDF-1 alpha, SDF-1 Beta, CD4, CD40L, TNF-RI, TNFRII, TARC, TECK, TGF alpha, TGFI BetaI, TGF Beta2, TGF Beta3, TNF beta/lymphotoxin, TNF-alpha, TPO, TRAIL, TWEAK, and VEGF.

In a preferred embodiment of the invention, the secretome of the invention comprises Caspase-3, EGF, G-CSF/CSF-3, GM-CSF, Granzyme B, HGF, ICAM-1, IL-10, MCP-1, MCP-2, MIP-1B, Osteopontin, PECAM, P-Selectin, SDF-1, TNF-α, VCAM-1, CD40L, FGF-2, GITRL, IFN-γ, IL-1a, MCP-2, PDGF-BB, TGF-β, TPO, VEGF-A, FGF-23, Gro-a, IL-1b, IL-2, IL-6, IL-7, IL-8, MCP-3, MIP-1a, RANTES, VEGF-D.

Table 1 below describes the concentration ranges obtained by the method of the invention using different factors as platelet agonists. The molecules analyzed were Caspase-3, EGF, G-CSF/CSF-3, GM-CSF, Granzyme B, HGF, ICAM-1, IL-10, MCP-1, MCP-2, MIP-1B, Osteopontin, PECAM, P-Selectin, SDF-1, TNF-α, VCAM-1, CD40L, FGF-2, GITRL, IFN-γ, IL-1a, MCP-2, PDGF-BB, TGF-β, TPO, VEGF-A, FGF-23, Gro-a, IL-1b, IL-2, IL-6, IL-7, IL-8, MCP-3, MIP-1α, RANTES, VEGF-D and are in the con-centration ranges described in Table 1.

In a preferred embodiment, the secretome of the invention is obtained using the platelet agonist TRAP6 at a concen-tration of 100 UM and comprises the molecules analyzed in the concentration ranges described in Table 1.

In another preferred embodiment, the secretome of the invention is obtained using the platelet agonist convulxin at a concentration of 0.625 ng/ml and comprises the molecules analyzed in the concentration ranges described in Table 1.

In another preferred embodiment, the secretome of the invention is obtained using the platelet agonist phorbol 12-myristate 13-acetate at a concentration of 100 ng/ml and comprises the molecules analyzed in the concentration ranges described in Table 1.

In another preferred embodiment, the secretome of the invention is obtained using the platelet agonist aggretin A at a concentration of 6.53 nM and comprises the molecules analyzed in the concentration ranges described in Table 1.

In another preferred embodiment the secretome of the invention is obtained using the platelet agonist collagen at a concentration of 30 μg/mL and comprises the molecules analyzed in the concentration ranges described in Table 1.

In another preferred embodiment the secretome of the invention is obtained using the platelet agonist collagen at a concentration of 90 μg/mL and comprises the molecules analyzed in the concentration ranges described in Table 1.

TABLE 1

| Human Platelet Secretome (HPS) (Range pg/ml). | | | | | | | |
|---|---|---|---|---|---|---|---|
| | Platelet Agonists* | | | | | | |
| FACTOR | U | TRAP6 | Col-30 | Col-90 | CVX | PMA | AggA |
| Caspase-3 | 65.5-398 | 126.6-360.3 | 150.6-317.7 | 168.2-380.2 | 137.7-326.4 | 110.1-883 | 124.6-285.4 |
| CD40L | 3.2-31.5 | 68.6-117.4 | 69.6-92.3 | 75.9-99.4 | 71.1-114.3 | 77.3-156.7 | 70.3-109.4 |
| EGF | 31.5-43.3 | 69.5-90.6 | 73.3-88.7 | 74.2-98 | 79.3-96.6 | 68.2-86 | 49.9-103.6 |

TABLE 1-continued

Human Platelet Secretome (HPS) (Range pg/ml).

| | Platelet Agonists* | | | | | | |
|---|---|---|---|---|---|---|---|
| FACTOR | U | TRAP6 | Col-30 | Col-90 | CVX | PMA | AggA |
| FGF-2 | 2.9 | 2.9 | 2.9 | 2.9 | 2.9 | 2.9-23.2 | 2.9 |
| FGF-23 | 252.7-511.5 | 548.5-912.7 | 567.8-882 | 570.8-1121.9 | 569.3-945.4 | 462.4-962.8 | 629-991.6 |
| G-CSF/CSF-3 | 87.2-200.7 | 221.1-404.3 | 235.1-414.8 | 244.2-544.7 | 239.7-448.6 | 154.2-468.7 | 258.2-438.6 |
| GITRL | 56-184.5 | 223.8-427.8 | 245.4-391.4 | 250.7-445.8 | 237.4-490 | 177.5-454.4 | 281.1-459.2 |
| GM-CSF | 71.7-152.6 | 181.9-296.1 | 191.4-269 | 196.6-341.1 | 186.1-316.2 | 147.5-307.6 | 211.4-332.8 |
| Granzyme B | 9.8-62 | 73.6-96.2 | 62-111 | 88.6-177.2 | 57.4-114.8 | 9.8-62 | 38.5-62 |
| Gro-α | 2.1-2.1 | 2.1-19.1 | 2.1-23.8 | 2.1-28.2 | 2.1-30 | 2.1-49.3 | 2.1 |
| HGF | 49-9-63.2 | 95.2-130.7 | 87.7-132 | 82.5-173.3 | 90.3-147.9 | 97-137.1 | 90.5-137.3 |
| ICAM-1 | 3022-5770 | 2655.6-4833 | 2303.9-4567 | 2207.7-4300.2 | 2332.4-4411 | 2679.5-4825.4 | 2661.6-5272.6 |
| IFN-γ | 6-35.5 | 47.1-85.9 | 51.7-85.1 | 46.8-99 | 49.2-103.9 | 27.4-92.7 | 55.2-86.6 |
| IL-10 | 1.8-14 | 14.2-26.1 | 16.9-22.4 | 15.2-25.5 | 14.1-31.7 | 7-26.7 | 16.4-27 |
| IL-1a | 0.7 | 0.7-9 | 0.7-7 | 0.7-8.6 | 0.7-9.3 | 0.7-10.5 | 0.7-10.4 |
| IL-1b | 12.3-31 | 41.3-80.3 | 41.8-68.1 | 40.8-91.7 | 40.3-90.1 | 27.9-88 | 50.2-71.1 |
| IL-2 | 133.3-169.1 | 180-227 | 170.7-209.4 | 175.4-245-4 | 170.3-231.4 | 163.5-232.6 | 191-246.1 |
| IL-6 | 8 | 24-51 | 10.4-36.9 | 18.2-54 | 10.4-57 | 8-60.2 | 11.8-34 |
| IL-7 | 17.3-32.6 | 33.3-43.9 | 31-41.8 | 36.6-41.4 | 35.3-40.9 | 35.2-44.1 | 31.8-43.8 |
| IL-8 | 2.4 | 2.4-2.4 | 2.4 | 2.4 | 2.4 | 2.4-15.8 | 2.4 |
| MCP-1 | 38.2-52.6 | 67.6-95 | 69.4-94.8 | 67.3-111.5 | 67-106.1 | 59.7-98.2 | 72-99.4 |
| MCP-2 | 69.1-135.7 | 172.8-294.5 | 105.3-265.1 | 126.1-263.3 | 206.5-317.7 | 255.5-384.6 | 149.9-318.9 |
| MCP-3 | 46.1-74.4 | 77-105.4 | 77-130.9 | 72.1-148.6 | 78.4-113.6 | 63.7-103.2 | 78.4-104.4 |
| MIP-1α | 1.7-11.9 | 12.8-22.3 | 12.6-19.7 | 11.9-23.9 | 13.8-23.9 | 10.1-25.5 | 16.5-21.7 |
| MIP-1β | 7.7 | 62.6-126.3 | 59.1-109.6 | 68.6-127.3 | 60.7-125.8 | 66.1-147.2 | 81.4-141 |
| Osteopontin | 11.8 | 11.8 | 11.8 | 11.8 | 11.8 | 11.8-72.1 | 11.8 |
| PDGF-BB | 271.6-5767.2 | 972.4-17119.7 | 766.3-16946.5 | 999.4-16063.6 | 941.2-18505.9 | 871.6-14389 | 957.1-18754.3 |
| PECAM (×10³) | 40-118.5 | 80.4-1817.9 | 70.8-1817.9 | 73.2-1817.9 | 72.5-1817.9 | 79.1-1817.9 | 76.8-1817.9 |
| P-Selectin (×10³) | 77.2-212.1 | 155.7-5523 | 138.5-5523 | 138.4-5523 | 145.7-5523 | 158.3-5523 | 152.2-5523 |
| RANTES | 46.4-116.3 | 57-129.5 | 64.3-128.1 | 67.6-126.2 | 59.1-99 | 62.3-600.2 | 53.4-106.2 |
| SDF-1 | 326.9-785.4 | 898.5-1307.2 | 815-1120.7 | 787.9-1132.2 | 827.7-1185 | 979.3-1673 | 959.1-1126.1 |
| TGF-β | 3462.6-4002.3 | 4750.7-6911.8 | 4732.2-5252.1 | 4371.4-5292.5 | 4649.1-6909.8 | 4645.2-5456.8 | 4347.8-6199 |
| TNF-α | 39.7-66.4 | 76-127.2 | 77.8-110.8 | 77.6-131.5 | 78-134.2 | 65.3-131.7 | 89.7-145.2 |
| TPO | 94-119.4 | 119.4-404.3 | 90.1-338.9 | 79.3-414.8 | 79.3-407.8 | 94-505.9 | 169.8-293.9 |
| VCAM-1 | 1551.9-2309.8 | 1489-2531.6 | 1442.9-2203.5 | 1530.4-2215.8 | 1465.9-2573.2 | 1652-2405.8 | 1685.6-2801.8 |
| VEGF-A | 75.3-105 | 185.3-239.2 | 164.9-214.2 | 165.7-248.1 | 157.3-290.1 | 179.9-292.5 | 157.6-292.3 |
| VEGF-D | 2.7-29.7 | 33.7-72.7 | 31.5-59.7 | 34.1-69.9 | 31.7-87.5 | 19.6-77.6 | 40.5-78.7 |

*The platelet agonists in the table are as followed: U—Unstimulated platelets; TRAP96—Thrombin receptor-activating peptide-6; Col-30 and Col-90—collagen at 30 μg/mL and 90 μg/mL, respectively; CVX—Convulxin; PMA—phorbol 12-myristate 13-acetate; AggA—aggretin A.

As mentioned previously, the composition of the secretome of the invention depends on the signaling cascades that are activated by the activating agents and on the origin and processing of the platelet rich sample from where the secretome of the invention is obtained. In cases where the secretome of the invention is obtained from a biological sample from a subject, the physiological state of the subject also determines the platelet reactivity and therefore will influence the final composition of the platelet derived secretome. Therefore, comparison of platelet derived secretomes of subjects with different physiological states, i.e. healthy subject versus subject with pathology, can be used in the determination of disease biomarkers. As such, another aspect of the present invention refers to a use in vitro of a method for identifying biomarkers for the diagnosis or prognosis of a disease, from here onwards the biomarker use of the invention, comprising:

a) obtaining the secretome of the invention from a subject; and b) comparing the platelet derived secretome from step a) with a control platelet derived secretome, wherein the presence, absence or the variation in level of a component of the secretome obtain in step a) compared to the control platelet derived secretome is indicative that said component is a biomarker.

The term "biomarker" as used herein refers to a substance, the presence of which can be objectively determined and quantified in the composition of the secretome of the invention by the methods described previously, which is used as an indicator of the presence/absence of the disease or the prognosis thereof. The disease biomarkers of the invention can be detected and/or quantified, meaning that one can only detect its presence/absence, only detect changes in its amount or concentration, or one can detect both its presence/absence and changes in its amount or concentration.

The term "diagnosis" as used herein refers to the procedure by which a certain disease, nosological entity, syndrome, or any health-disease condition is identified by analyzing a series of clinical parameters or symptoms characteristic of said disease, and which distinguish it from other diseases with similar clinical pictures. By "diagnosis" is also intended to refer to the providing of information useful for diagnosis.

The term "prognosis" as used herein refers to the procedure by which the probability or possibility of a subject developing a certain disease, nosological entity, syndrome, or any health-disease condition is determined by analyzing a series of clinical parameters or symptoms characteristic of said disease, and which distinguish it from other diseases with similar clinical pictures. As will be understood by those skilled in the art, such a prognostic assessment, although preferred to be, may not normally be correct for 100% of the subjects to be prognosed. The term, however, requires that a statistically significant portion of the subjects can be identified as having the disease or being predisposed to the disease. The number that is statistically significant can be established by one skilled in the art by use of different statistical tools, for example, but not limited to, by determination of confidence intervals, determination of P-significance value, Student's test or Fisher's discriminant functions, Mann Whitney nonparametric measures, Spearman correlation, logistic regression, linear regression, area under the ROC curve (AUC). Preferably, the confidence intervals are at least 90%, at least 95%, at least 97%, at least 98% or at least 99%. Preferably, the p value is less than 0.1, less than 0.05, less than 0.01, less than 0.005 or less than 0.0001. Preferably, the present invention makes it possible to correctly predict the disease differentially in at least 70%, more preferably in at least 80%, much more preferably in at least 90% of the subjects of a given group or population analyzed.

The term "subject" as used herein refers to an animal, preferably a human of any age and gender. Therefore, in a preferred use of the biomarker of the invention, the subject is an animal, preferably a human.

The expression "comparing the platelet derived secretome from step a) with a control platelet derived secretome" of step b) of the biomarker use of the invention, refers to the process of comparing two platelet derived secretomes obtained by the method of the invention, wherein one platelet derived secretome is obtained from a subject which suffers, may suffer or will suffer of a certain disease, nosological entity, syndrome, or any health-disease condition, and the other platelet derived secretome is obtained from a healthy subject. Both secretomes can be obtained from the same or different subjects at different stages of a certain disease, nosological entity, syndrome, or any health-disease condition, or the same subject in a healthy condition versus affected by a disease/condition/syndrome. The expression "wherein the presence, absence or the variation in concentration of a component of the secretome obtain in step a) compared to the control platelet derived secretome is indicative that said component is a biomarker" refers to the process of analyzing or comparing the platelet derived secretomes obtain in step a) with the control platelet derived secretome, wherein said analysis, comparison may identify components whose present or absence changes from one secretome to another, or components whose concentration varies from one secretome to another, indicating that these components are affected by the disease, nosological entity, syndrome, or health-disease condition which is being analyzed, and are therefore biomarkers for said condition.

Examples of diseases biomarkers that can be identified are biomarkers for vascular disorders, blood cancers, immune disorders, coagulation disorders, pain modulation disorders. In a preferred embodiment, the disease biomarkers of the invention are selected from a list of diseases consisting of: erythromelalgia, peripheral artery disease, renal artery stenosis, Buerger's disease, Raynaud's disease, disseminated intravascular coagulation, cerebrovascular disease, acute lymphoblastic leukemia, chronic lymphocytic leukemia, acute myelogenous leukemia, chronic myelogenous leukemia, hairy cell leukemia, T-cell prolymphocytic leukemia, juvenile myelomonocytic leukemia, systemic lupus erythematous, scleroderma, hemolytic anemia, vasculitis, Type 1 diabetes, Graves' disease, rheumatoid arthritis, osteoarthritis, psoriatic arthritis, Goodpasture syndrome, pernicious anemia, myopathy, lyme disease, thrombophilia, coagulopathy, acute traumatic coagulopathy, sensory modulation disorder, atherosclerosis, inflammatory bowel disease, Alzheimer's, ankylosing spondylitis, asthma, Crohn's disease, colitis, dermatitis, diverticulitis, fibromyalgia, hepatitis, nephritis, Parkinson's disease, skin disorders and ulcerative colitis.

As mentioned previously, the secretome of the invention has a complex composition being particularly rich in growth factors. As such, the secretome of the invention is of particularly useful as a culture medium and/or culture medium supplement. Therefore, another aspect of the invention relates to the use of the secretome of the invention as culture medium and/or culture medium supplement for in vitro and/or ex vivo cell culture and/or tissue cultures, preferably stem cells cultures, fibroblasts primary cultures, fibroblast cultures, dendritic cells cultures, other immune cells and cell lines. Said cultures maybe be for research purposes as well as cell therapy purposes.

The expression "culture medium supplement" as used herein refers to a medium additive which is added to the medium to maintain cell viability and/or stimulate the proliferation and/or migration of the cells.

The terms "cell culture" and "tissue culture" refer to the maintenance and propagation of cells and cells in tissues, preferably of animal origin (including human derived cells) in vitro.

The term "maintenance of cells" as used herein refers to the keeping of cells in optimal conditions. The term "proliferation of cells" refers to the multiplication of cells thereby leading to an increase in the cell number. The term "migration of cells" refers to a central process in the development and maintenance of multicellular organisms that require the orchestrated movement of cells in particular directions to specific locations i.e. tissue formation during embryonic development, wound healing and immune responses.

Pharmaceutical Compositions

As aforementioned, the secretome of the invention is rich in growth factors which can be used to stimulate the growth of cells in vitro. Likewise, such stimulation capabilities can also be used in vivo, and as such the secretome of the invention has uses in regenerative medicine and treatment of tissue damage. Hence, another aspect of the invention relates to a pharmaceutical composition comprising the secretome of the invention, from here onwards the pharmaceutical composition of the invention. Another aspect of the invention relates to the pharmaceutical composition of the invention for use in regenerative medicine and/or the treatment of tissue damage.

The term "regenerative medicine" as used herein refers to the process of replacing or regenerating cells, tissues, or organs to restore or establish their normal function.

The term "treatment" as used herein refers to fighting the effects caused as a consequence of the disease or pathological condition of interest (like tissue damage) in a subject (preferably a mammal and, more preferably, a human), including:

i) inhibiting the disease or pathological condition, i.e., stopping its development;

(ii) alleviating the disease or pathological condition, i.e. causing the regression of the disease or pathological condition or its symptoms;

(iii) stabilizing the disease or pathological state.

In a preferred embodiment of the invention, the pharmaceutical composition of the invention is used in the treatment of a disease selected from a list consisting of but not limited to: erythromelalgia, peripheral artery disease, renal artery stenosis, Buerger's disease, Raynaud's disease, disseminated intravascular coagulation, cerebrovascular disease, acute lymphoblastic leukemia, chronic lymphocytic leukemia, acute myelogenous leukemia, chronic myelogenous leukemia, hairy cell leukemia, T-cell prolymphocytic leukemia, juvenile myelomonocytic leukemia, systemic lupus erythematous, scleroderma, hemolytic anemia, vasculitis, Type 1 diabetes, Graves' disease, rheumatoid arthritis, osteoarthritis, psoriatic arthritis, Goodpasture syndrome, pernicious anemia, myopathy, lyme disease, thrombophilia, coagulopathy, acute traumatic coagulopathy, sensory modulation disorder, atherosclerosis, inflammatory bowel disease, Alzheimer's, ankylosing spondylitis, asthma, Crohn's disease, colitis, dermatitis, diverticulitis, fibromyalgia, hepatitis, nephritis, Parkinson's disease, skin disorders, and ulcerative colitis, or any pathological manifestations that require wound healing or tissue regeneration, shortening healing times, or aiding in resolving the lesion.

In another preferred embodiment of the pharmaceutical composition of the invention, the secretome of the invention is fresh, frozen, lyophilized, encapsulated or nanoencapsulated.

In yet another preferred embodiment of the pharmaceutical composition of the invention, the platelet derived secretome is an animal platelet derived secretome, preferably a mammal platelet derived secretome, more preferably a human platelet derived secretome.

In a preferred embodiment, the pharmaceutical composition of the invention further comprises an acceptable pharmaceutical adjuvant, an acceptable pharmaceutical vehicle, and/or another active ingredient.

The expression "acceptable pharmaceutical adjuvant", as used herein, refers to a substance which assists in the absorption of the elements of the pharmaceutical composition of the invention, stabilizes such elements, activates or assists in the preparation of the composition in the sense of giving it consistency or providing flavors that make it more pleasant. Thus, the excipients or adjuvants could have the function of keeping the ingredients together, as for example in the case of starches, sugars or celluloses, the function of sweetening, the function of coloring, the function of protecting the composition, as for example to insulate it from air and/or humidity, the function of filling a tablet, capsule or any other form of presentation, a disintegrating function to facilitate the dissolution of the components and their absorption in the intestine, without excluding other types of excipients not mentioned in this paragraph.

The expression "acceptable pharmaceutical vehicle", as used herein, refers to a substance used in the composition to dilute any of its constituent parts to a certain volume or weight. The pharmaceutically acceptable vehicle is a substance that is inert or has an identical action to any of the elements included in the pharmaceutical composition of the invention. The function of the vehicle is to facilitate the incorporation of other elements, to allow a better dosage and administration or to give consistency and form to the composition.

The term "active ingredient" refers to a therapeutically active compound, such as serum or plasma, as well as to any prodrugs thereof and the pharmaceutically acceptable salts, hydrates and solvates of the compound and the prodrugs.

The composition of the present invention may also take the form of a sustained release drug formulation or any other conventional release system, such as nanoparticles, liposomes or nanospheres, polymeric material, biodegradable or non-biodegradable implant or biodegradable microparticles, such as biodegradable microspheres. This composition and/or its formulations can be administered to an animal, and therefore to humans, in various ways, including intraperitoneal, intravenous, intradermal, intraspinal, intrastromal, intra-articular and intrasynovial, intrathecal, intralesional, intra-arterial, intramuscular, intranasal, intracranial, subcutaneous, intra-orbital, intracapsular, topical, oral, through transdermal patches, percutaneous, nasal spray, surgical implant, internal surgical paint or infusion pump.

The administration of the pharmaceutical composition of the invention shall be carried out in a therapeutically effective dose, which is sufficient to demonstrate a benefit for the patient. Such a benefit may involve the improvement of at least one symptom related to the disease or pathology that affects the patient. The prescription of the treatment, that is to say, the decisions about the doses, periodicity, duration, etc., will fall under the responsibility of the general practitioner or the specialist who attends the affected patient.

The term "therapeutically effective dose" or "therapeutically effective amount", as used in the present invention, refers to an amount (or amount per unit mass of the individual to whom it is administered) of a drug or therapeutic agent that causes a detectable therapeutic effect on an individual or a group of individuals to whom it is administered, causing minimal side effects or toxicity. The therapeutically effective amount useful to produce a therapeutic effect can be determined by conventional techniques well known to specialists in the technique. The term "therapeutically effective dosage-50" or "therapeutically effective dosage-95" includes a statistical value in which the therapeutic effect must be detectable in 50% or 95% of the individuals to whom it is administered. With regard to the toxic effects of the drug or compound, it is preferable that the effective therapeutic dose does not cause any. However, although toxic effects may sometimes occur, a compromise may be reached in which these are considered preferable to the normal development of the disease or pathology without the administration of the drug or compound and may in turn be treated by additional therapies.

EXAMPLES

Figure 1A:
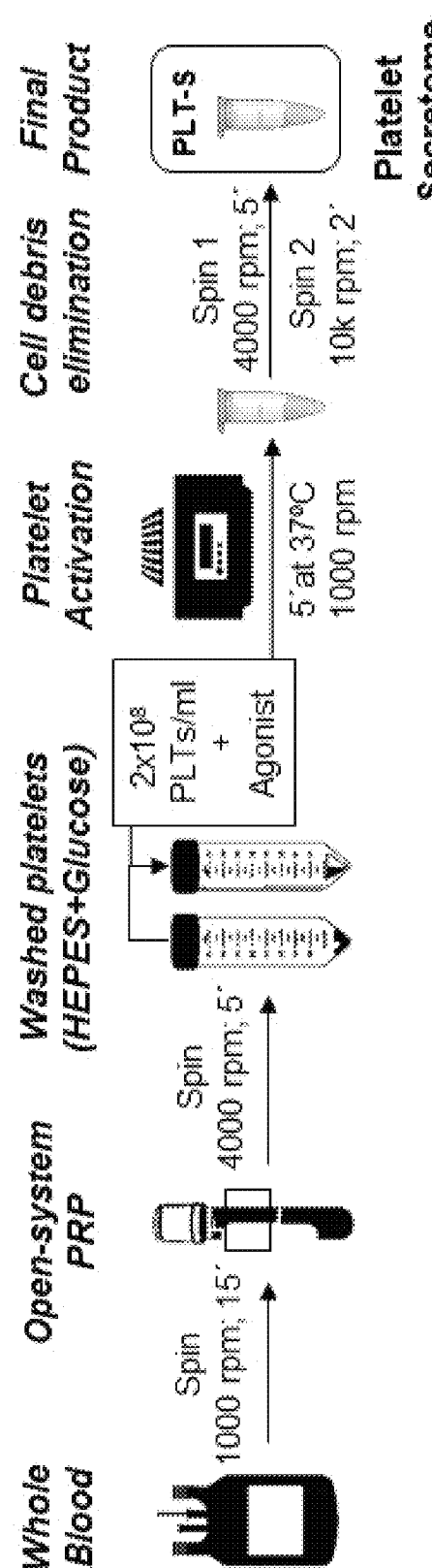
FIG. 1. A. Example of a workflow of secretome preparation. B. Heat map depicting the hierarchical clustering of secretome samples based on their differential composition. C. Cluster dendrogram and Principal Component Analysis (PCA) of secretome samples. The average of secretomes from 4 different donors is used. D. Degranulation analysis by flow cytometry, of platelets stimulated with different agonists.
Figure 1B:
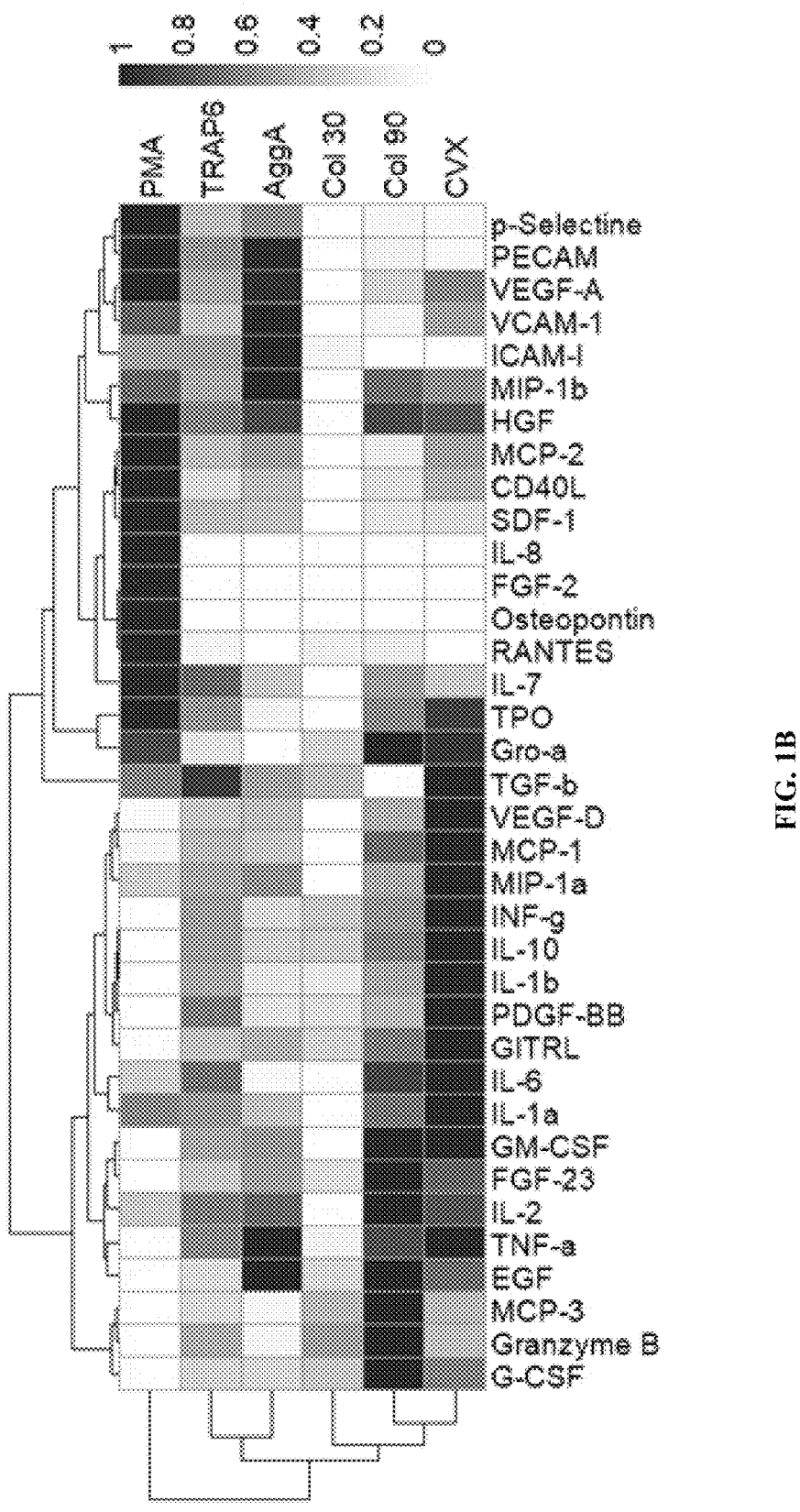
Figure 1C:
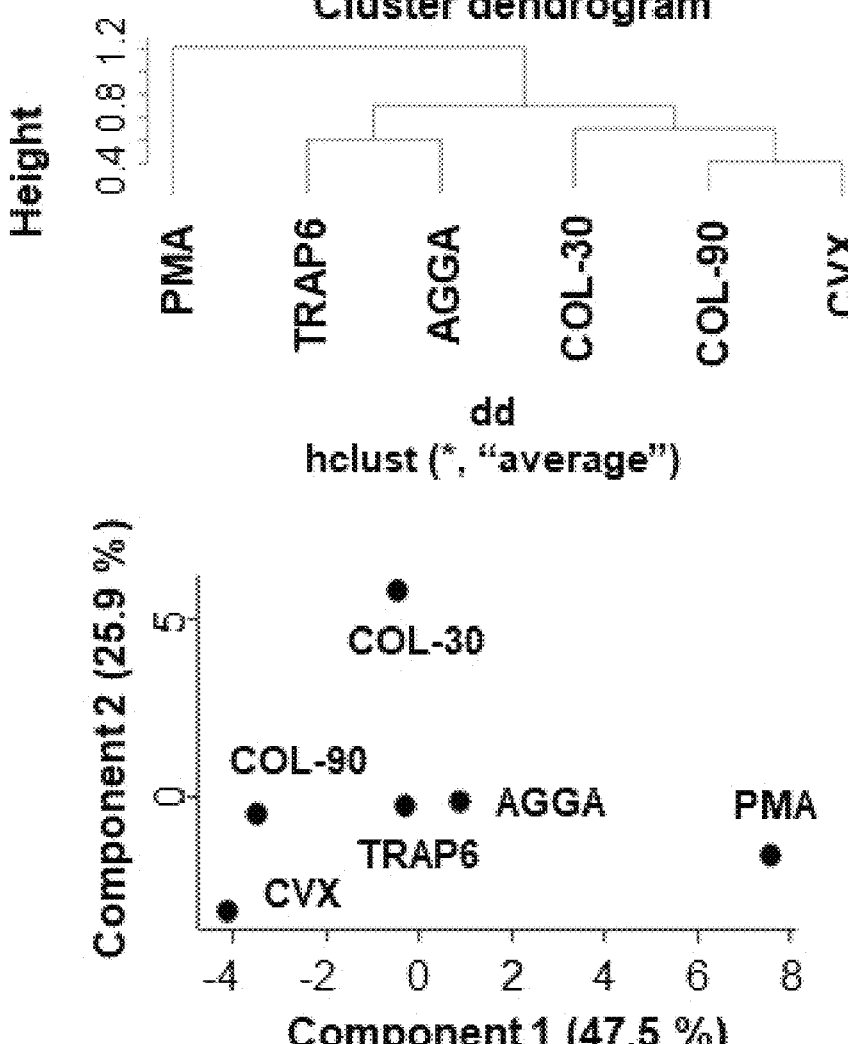
Figure 1D:
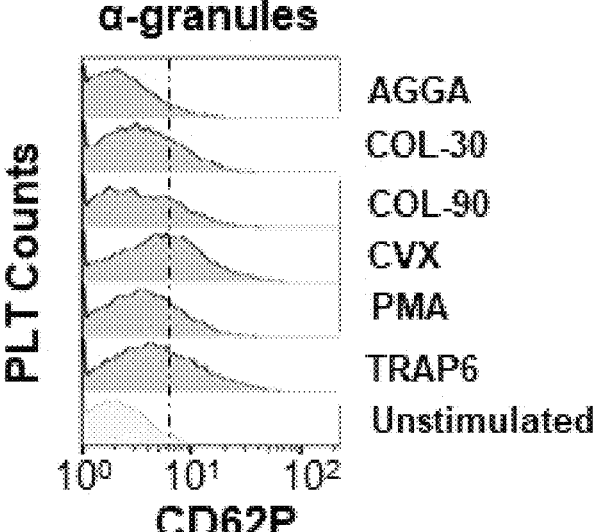
Figure 1D:
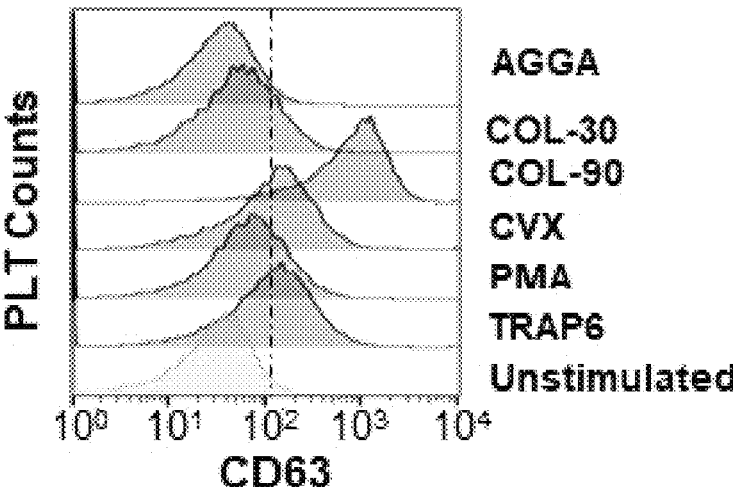
Figure 2:
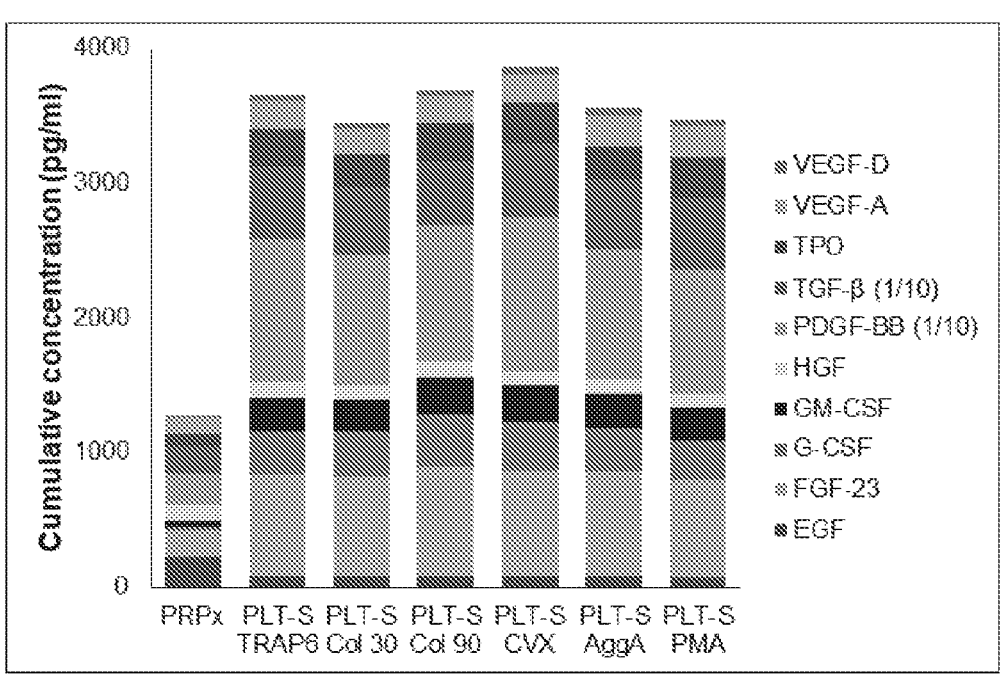
FIG. 2. Bar graphs depicting the cumulative sum of growth factor concentration in PRP samples and in secretome samples (different agonists). The concentration is higher in secretomes, compared to PRP, even if the platelet count (average) is lower.
Figure 3:
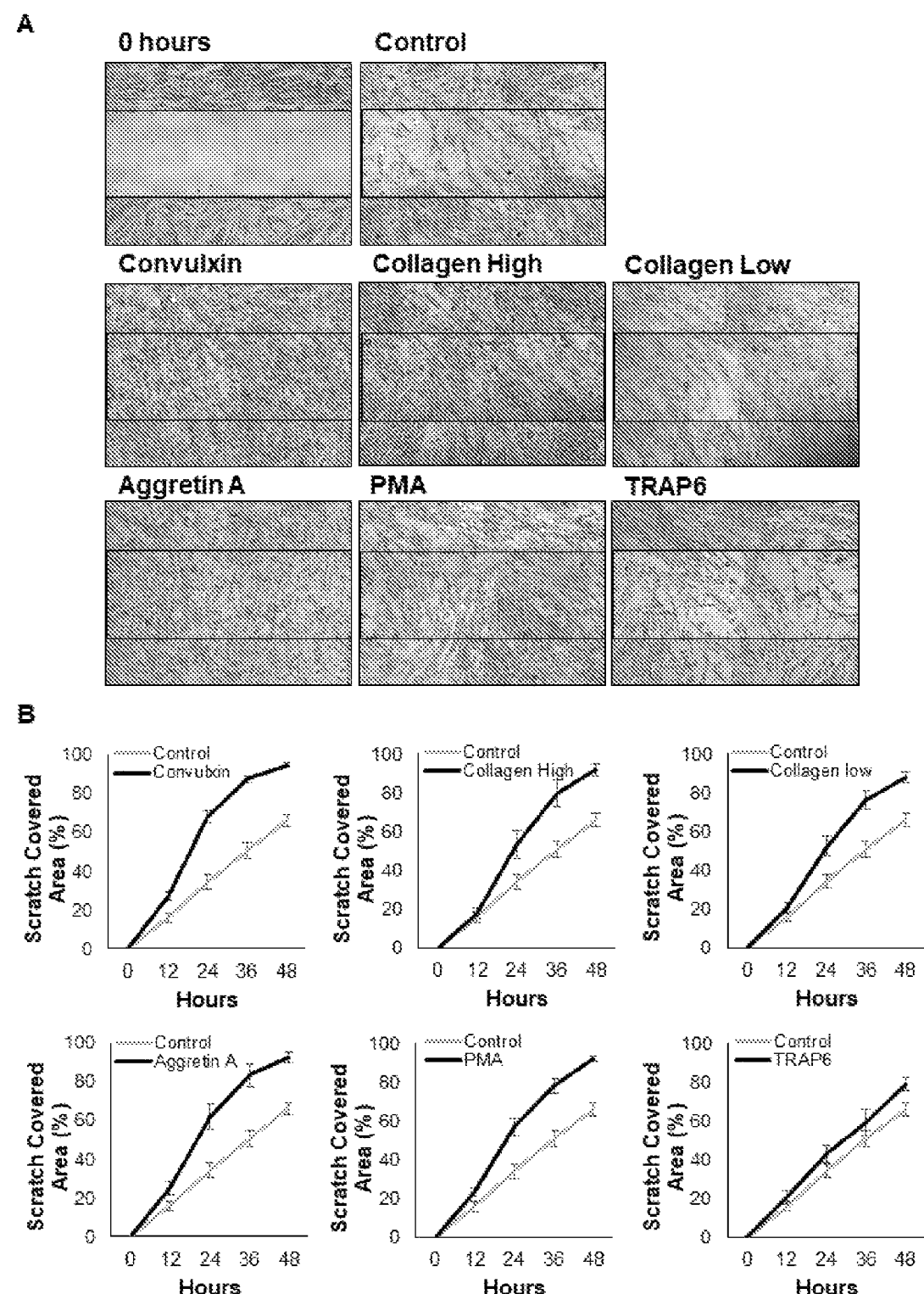
FIG. 3. Wound healing assay and scratch closure monitoring over time. MRC-5 cells were stimulated with Secretomes (10%, n=6), in addition to 10% fetal bovine serum (FBS), as standard culture conditions). A. Representative images of the scratch at the beginning of the assay and 48 h after the stimulation are shown. B. The graph depicting the closing dynamic of MRC-5 cells stimulated with the different secretomes compared with control (standard culture conditions).
Figure 4:
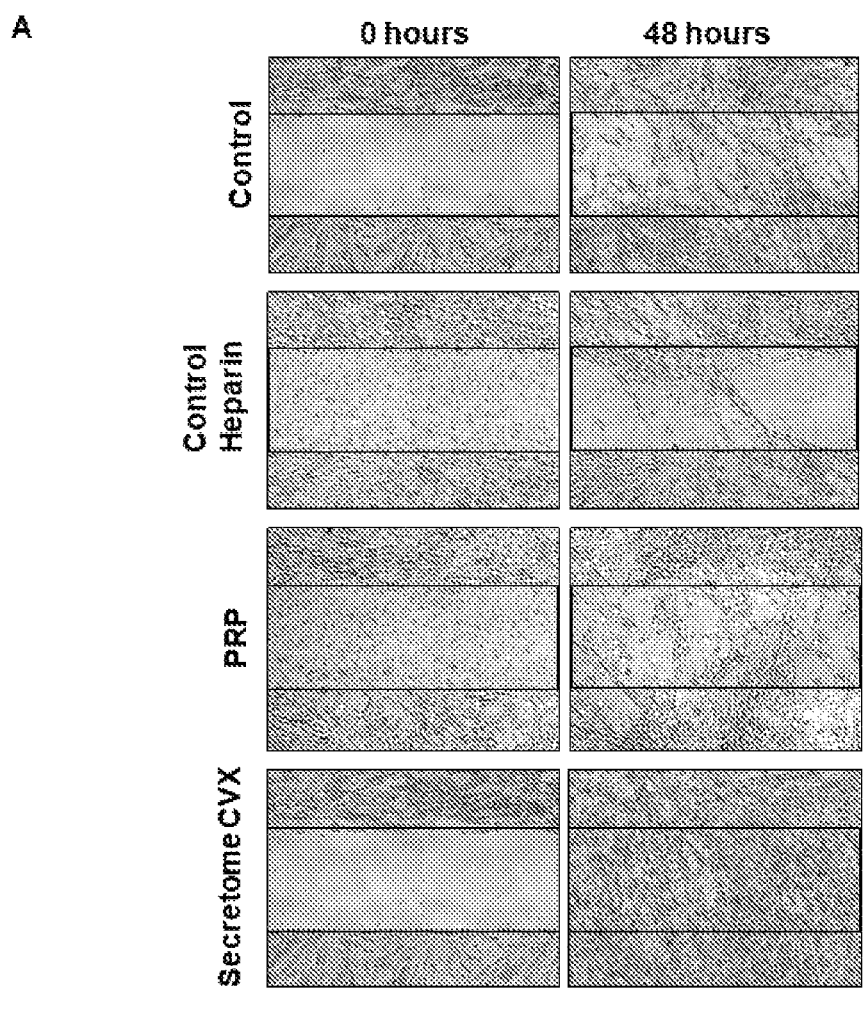
FIG. 4. Comparison of the in vitro regenerative capacity between platelet-rich plasma (PRP) and platelet secretomes (PLT-S). A scratch wound healing assay was performed on MRC-5 cells treated stimulated or not with 10% PRP or secretomes (in addition to 10% FBS, standard culture conditions) to determine cell proliferation capacity. A. Showing scratch wounds in MRC-5 cells at time 0 h and representing wound status 48 h after the initiation of the scratch when the cells were treated with PRP or secretome (obtained with convulxin). B. The graph depicting the closing dynamic of PRP or secretome stimulated MRC-5 cells compared to their respective control condition (standard culture media w/o heparin).
Figure 4:
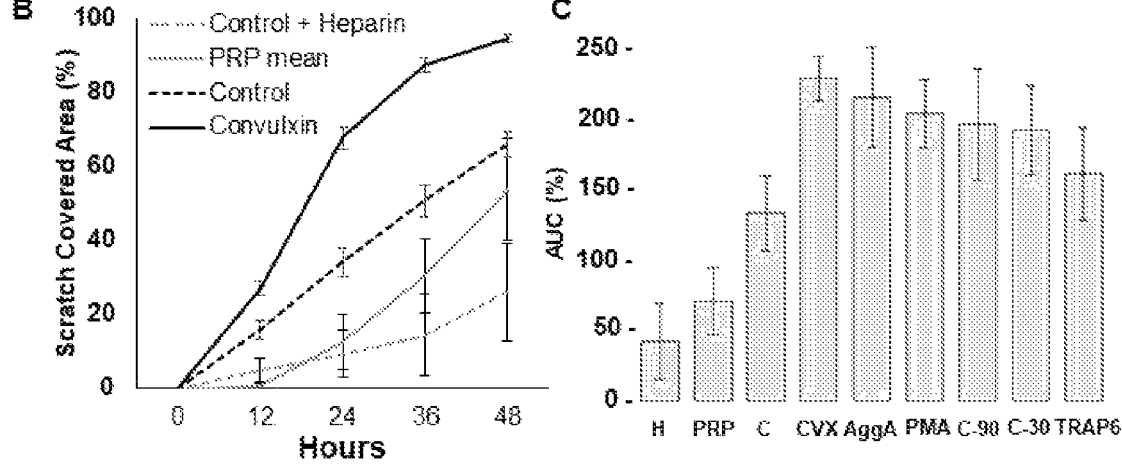

Materials and Methods
PRP Preparation Using a Closed-System
Platelet-Rich Plasma (PRP) was Obtained from Interrupted Blood Donations (n=14) as described in Ojea-Pérez A. M. et al, 2019, Transfus Apher Sci., 58 (5), 701-704. The fractionation was done using the equipment of a certified blood bank (Centro Comunitario de Sangre y Tejidos de Asturias—CCSTA). In brief, a double differential centrifugation was done after connecting the blood bag to collecting pediatric bags: first one at 1130 rpm for 5 min without brake, after which the plasma fraction containing platelets is separated from the red blood cells with a press Compomat® G5 (Fresenius-Kabi) system into a separate bag. The second centrifugation is performed at 2500 rpm for 12 min and break 4, which allows the separation of PRP into a new bag and then distributed into 3 pediatric bags (approximately 10 mL each). PRP samples were placed at −40° C. to allow platelet lysis and storage. Frozen samples (PRPx) were thawed in a 37° C. water bath and centrifuged at 10 krpm for 2 minutes to eliminate cell debris. The supernatant of frozen-thawn PRPx samples was collected for further use.
Platelet Secretome (PLT-S) Preparation
PLT-S was prepared from whole blood (interrupted donations), centrifuged at 1000 rpm for 15 minutes followed by PRP collection (open system). The concentration of platelets in PRP was measured using a CBC analyser (Sysmex XN-10/XN-20 Hematology Analyzer). The PRP was then centrifuged at 4000 rpm for 5 minutes and the platelet-poor plasma (PPP) supernatant was then removed. HEPES Glucose Buffer (132 mM NaCl, 6 mM KCl, 1 mM MgSO4, 1.2 mM KH2PO4, 20 mM HEPES, pH 7.4, containing 5 mM D-glucose) was used to re-suspend the platelet pellet to a concentration of $2 \times 10^8$ platelets/mL. Then, platelets were activated using a PAR1 agonist (TRAP6; 100 UM; BACHEM H-8365.0005), convulxin (0.625 ng/ml; ENZO Life Sciences ALX-350-100-C050), phorbol 12-myristate 13-acetate (PMA; 100 ng/ml; Sigma-Aldrich P8139-5 MG), aggretin A (6.53 nM, kind gift of Prof. J. Eble), collagen (30 μg/mL and 90 μg/mL; Sigma-Aaldrich C4243-20ML), under constant shaking during 5 minutes at 37° C. using a Thermomixer® (Mixing Block MB-102; BIOER). Unlike other published studies we did not stop the reaction incubating the platelets on ice. Finally, platelets were centrifuged at 10.000 rpm for 2 minutes to eliminate cell debris. The secretome supernatant was collected and filtered with a 0.22 μm pore filter, divided into aliquots and frozen at −80° C. for further use. Alternatively, after counting and re-suspending in HEPES Glucose Buffer, platelets were stored at −80° C. to allow the complete rupture of platelets (i.e., platelet lysate).
Quality Control: Degranulation and 33 Integrin Activation Analysis
Platelets were stimulated as described above (secretome preparation) and incubated with a panel of surface markers (CD9-Alexa Fluor® 647; CD62P-PE; CD63-PECy7) and conjugated fibrinogen FBG-Alexa Fluor® 488), before and after stimulation, to analyze platelet degranulation capacity and B3 integrin activation upon stimulation. This analysis would serve as our quality control of prepared secretomes prior to multiplex analysis. After incubation, platelets were analyzed by flow cytometry. Platelets were gated based on forward/side scatter and CD9 positivity. The cut-off was set on unstimulated samples and the increase of CD62p and CD63 expression and fibrinogen binding was measured. Samples were selected for further analysis, when platelet degranulation was optimal (i.e., no degranulation or FBG binding without stimulus, and proper degranulation and FBG binding upon stimulus). All the antibodies were from BD Biosciences. Data were acquired on a FACS Aria II™ flow cytometer (BD Biosciences) and analyzed using FlowJo™ software (Tree Star, Ashland, OR, USA).

Multiplex Immunoassay

Growth factors, cytokines, chemokines and immuno-modulator molecules contained in the different platelet bio-products were measured by using high-performance multi-plex immunoassay with the Human Procartaplex™ (Invitrogen, Carlsbad, CA, USA). This array is an antibody-based magnetic bead system that allow the quantitation of a wide range of biomarkers using the Luminex® 200 instrument platform (Luminex Corporation, USA). The multiplex assay was performed following the manufacturer's instructions and the plates were read using the xPONENT® software (Luminex Corporation, USA). The specific factors analysed were: Caspase-3, CD40L, EGF, FGF-2, FGF-23, G-CSF (CSF-3), GM-CSF, GITRL, Granzyme B, GROα (KC/CXCL1), HGF, ICAM-1, IFNγ, IL-1α, IL-1β, IL-2, IL-6, IL-7, IL-8 (CXCL8), IL-10, MIP-1a (CCL3), MCP-1 (CCL2), MCP-2 (CCL8), MCP-3 (CCL7), MIP-1β (CCL4), Osteopontin, PDGF-BB, PECAM-1, P-Selectin, RANTES (CCL5), SDF-1α, Thrombopoietin (TPO), TGFβ, TNFα, VCAM, VEGF-A and VEGF-D.

Scratch Wound Closure Assay and Image Analysis

To analyse the regenerative potential of PLT-S or PRP, the scratch wound closure assays were performed with the MRC-5 fibroblast cell line. MRC-5 cells were seeded within Culture-Insert 2 well 24 ibiTreat (μ-Plate 24 Well Black, Ibidi), at $3.5 \times 10^5$ cells/mL (70 μL volume per well per chamber) and incubate for cell attachment until reach 80-90% confluence (approximately 24 hours), and then the silicone insert was carefully removed, leaving a 500 μm cell-free gap (according to manufacturer). After washing away any non-adherent cells, culture media supplemented with 10% of PLT-S or PRP (in addition to 10% fetal bovin serum—FBS—) was added to the cell culture. To observe wound closure, plates were monitored for 48 h using a time-lapse microscopy Zeiss AxioObserver Z1 microscope (Carl Zeiss, Germany) equipped with a 'stage incubator' where temperature and the atmosphere were kept at 37° C. and 5% CO2, respectively. Imaging was performed with a Plan-Apochromat 10x/0,45 M27 (dt=2.1 mm) objective. Mosaic images (3×3) were taken using a camera (AxioCam MRm; Carl Zeiss) every 12 hours. Fields were selected with micrometric precision (in a three-dimensional manner, axes xyz) using the Tiles tool (z-position from Tiles setup) from ZEN Blue software (Carl Zeiss).

The images were subsequently analyzed using Fiji/ImageJ software (NIH) with the Montpellier Ressources Imagerie (MRI) Wound healing tool macro available online at github.com/MontpellierRessourcesImagerie/imagej_macros_and_scripts/wiki/Wound-Healing-Tool. The plugging analysed the area of a wound in a cellular tissue on a stack of images representing a time-series that measured the reduction in cleared space between the wound edges. Percentage of gap closure was calculated and compared between controls and treatment groups.

Statistical Analysis.

All data were calculated and expressed as mean±standard error of the mean (SEM). A P-value of >0.05 was considered statistically significant. Data were evaluated using analysis of variance (anova) with Tukey's HSD (honest significant difference) tests for multiple comparisons. Statistical analysis and heatmaps were performed with R package (Rstudio®) version 3.5.2. Principal Component Analysis (PCA)

was performed after scale to interval normalization of variable values using Perseus Software version 1.6.7.0.

Example 1—the Platelet Secretion Profile is Determined by the Activation Signaling Pathway/the Platelet Derived Secretome Composition can be Modulated by the Stimulation of Platelets with Different Receptor Agonists We use washed platelets to generate plasma-free platelet secretomes. For this purpose, platelets from healthy donors (n=4) were stimulated with several receptor agonists (see material and methods) and then, a total of 37 factors, including growth factors, cytokines, chemokines and some immune mediators, were quantified using a multiplex human immunoassay. Prior the characterization by multiplex, we measured platelet activation using flow cytometry analysis of the expression of CD62p (alpha-granules), CD63 (dense granules and lysosomes) and fibrinogen as quality control of cargo degranulation.

The protein characterization showed a different secretion pattern that depends on the agonist-induced activation of platelets.

Next, PCA was performed on all multiplex variables in order to visualize the clustering of releasate samples, after normalizing data to interval (as described in M&M). This analysis revealed that the secretion profile of TRAP6 clustered with collagen (low dose), and Aggretin A, that the secretion profile of convulxin clustered with collagen (high dose), and PMA secretome was slightly distant to the rest.

Example 2—the Platelet Derive Secretome is More Enriched in Growth Factors than the Classical PRP We next compared the composition of PLT-S($200 \times 10^3$ PLTs/μl) with the composition of PRPx (PLT range 262-$728 \times 10^3$ PLTs/μl). We observed that most of the analytes were higher in concentration in PLT-S compared to PRP, even considering that PRP samples have a higher platelet density. In a striking way, the main growth factors involved in tissue regeneration such as FGF, VEGF, HGF and PDGF-BB, among others, were higher in concentration in PLT-S samples. Of note, the concentration of EGF showed a wide range (HPS 49,938 to 103,581; PRPx 90,424 to 472,029) and was the only factor showing a strong correlation with platelet number on each PRPx sample (r=0.82).

In the same way, cytokines, chemokines and the adhesion molecules PECAM1 (CD31) and P-selectin were detected in greater proportion in PLT-S samples. Contrariwise, ICAM-1 and VCAM-1 were detected in higher proportion in PRPx samples, as well as RANTES (188-fold), Caspase-3 (12-fold), and osteopontin (not detected in PLT-S samples) which englobe certain immune mediators and adhesion molecules that are mainly present in the plasma fraction.

Example 3—the Regenerative Capacity of the Platelet Secretomes is Different Depending on the Agonist Used to Induce Platelet Degranulation In order to evaluate the in vitro regenerative potential of PLT-S, we performed wound healing assays in MRC-5 cells (fibroblast) stimulated or not with the different PLT-S and the gap/wound closure was monitored over a period of 48 hours using a Time-Lapse microscope. Our results show that the wound closure dynamic is highly dependent on the composition of the bioproduct which in turn depends on the agonist used to activate the platelet cargo degranulation. The secretome obtained through the stimulation of GPVI by Convulxin has resulted in the most mitogenic response, achieving a 95% of wound closure compared to the 66% from the control. Similar results were obtained with Collagen high dose (90 µg/mL). In addition, the secretomes obtained with PMA and Aggretin A showed the same regenerative capacity, expressed in both cases as 92% of wound closure. Finally, the secretome obtained with TRAP6 had the lowest regenerative potential. Overall, these results are of highly relevance indicating the potential of using secretomes as treatment for regenerative purposes.

TABLE 2

| | | | | % Scracth | | | |
|---|---|---|---|---|---|---|---|
| | Control | Convulxin | TRAP6 | Collagen low | Collagen High | Aggretin A | PMA |
| Closure | | | | | | | |
| 0 h | 0.00 | 0.00 | 0.00 | 0.00 | 0.00 | 0.00 | 0.00 |
| 12 h | 15.88 | 27.06 | 20.26 | 20.53 | 18.06 | 25.16 | 23.65 |
| 24 h | 34.18 | 67.74 | 42.83 | 52.36 | 53.45 | 61.69 | 56.88 |
| 36 h | 50.70 | 87.34 | 59.05 | 76.01 | 79.68 | 83.18 | 78.12 |
| 48 h | 65.99 | 94.72 | 78.89 | 87.57 | 91.99 | 92.38 | 92.08 |
| SEM | | | | | | | |
| 0 h | 0.00 | 0.00 | 0.00 | 0.00 | 0.00 | 0.00 | 0.00 |
| 12 h | 2.51 | 1.88 | 3.37 | 2.52 | 2.67 | 3.45 | 2.03 |
| 24 h | 3.73 | 3.01 | 4.51 | 4.97 | 7.33 | 6.43 | 4.41 |
| 36 h | 4.10 | 1.94 | 6.71 | 4.61 | 7.00 | 5.98 | 3.71 |
| 48 h | 3.32 | 1.00 | 3.15 | 2.65 | 3.06 | 2.56 | 1.51 |

Wound closure (%): Mean experimental replicates and standard error of the mean (SEM) (n = 6). The table summarized the results obtained in wound healing assays.

TABLE 3

Tukey's honest significance test applicated to wound healing results obtained with Platelet Secretomes.

| | 12 hours | 24 hours | 36 hours | 48 hours |
|---|---|---|---|---|
| AGGA-C | 0.2766 | 0.0055 | 0.0011 | 0.0000 |
| Collagen High-C | 0.9991 | 0.1158 | 0.0046 | 0.0000 |
| Collagen Low-C | 0.9088 | 0.1232 | 0.0119 | 0.0000 |
| CVX-C | 0.0783 | 0.0002 | 0.0001 | 0.0000 |
| PMA-C | 0.4354 | 0.0239 | 0.0050 | 0.0000 |
| TRAP6-C | 0.9320 | 0.8789 | 0.9127 | 0.0124 |
| Collagen High-AGGA | 0.6556 | 0.9375 | 0.9997 | 1.0000 |
| Collagen Low-AGGA | 0.9295 | 0.8629 | 0.9686 | 0.8781 |
| CVX-AGGA | 0.9996 | 0.9850 | 0.9988 | 0.9978 |
| PMA-AGGA | 0.9999 | 0.9962 | 0.9959 | 1.0000 |
| TRAP6-AGGA | 0.9071 | 0.1313 | 0.0292 | 0.0127 |
| Collagen Low-Collagen High | 0.9980 | 1.0000 | 0.9995 | 0.9184 |
| CVX-Collagen High | 0.3118 | 0.4297 | 0.9552 | 0.9942 |
| PMA-Collagen High | 0.8331 | 0.9996 | 1.0000 | 1.0000 |
| TRAP6-Collagen High | 0.9991 | 0.7668 | 0.0949 | 0.0171 |
| CVX-Collagen Low | 0.6484 | 0.2821 | 0.6943 | 0.4433 |
| PMA-Collagen Low | 0.9894 | 0.9966 | 1.0000 | 0.8875 |
| TRAP6-Collagen Low | 1.0000 | 0.8157 | 0.2156 | 0.2160 |
| PMA-CVX | 0.9820 | 0.6998 | 0.8628 | 0.9937 |
| TRAP6-CVX | 0.6010 | 0.0096 | 0.0035 | 0.0011 |
| TRAP6-PMA | 0.9827 | 0.3910 | 0.1152 | 0.0099 |

*p > 0.05; p > 0.01; *p > 0.001

Example 4—the Regenerative Capacity of the Platelet Secretomes is Superior than the Classical PRP Images of the scratch wounds on human fibroblast (hF) monolayers (MRC-5 cell line) were captured 0 and 48 hours after scratching to show that hF proliferation into the scratch wound area was accelerated in the presence of PLT-S compared to PRP.

TABLE 4

Tukey's honest significance test applicated to wound healing results obtained with Platelet Secretomes and PRP.

| p-value | 12 hours | 24 hours | 36 hours | 48 hours |
|---|---|---|---|---|
| H-C | 0.05306299 | 0.01579964 | 0.00495476 | 0.00126844 |
| CVX-C | 0.00633986 | 1.6304E−05 | 0.00030073 | 0.0055908 |
| PRP-C | 2.7844E−06 | 0.00135844 | 0.05428079 | 0.40781981 |
| CVX-H | 5.6811E−06 | 7.9485E−09 | 2.2366E−08 | 6.4024E−08 |

TABLE 4-continued

Tukey's honest significance test applicated to wound healing results obtained with Platelet Secretomes and PRP.

| p-value | 12 hours | 24 hours | 36 hours | 48 hours |
|---|---|---|---|---|
| PRP-H | 0.75372194 | 0.98377852 | 0.27288598 | 0.01417463 |
| PRP-CVX | 2.534E−12 | 1.1162E−12 | 7.791E−10 | 8.8765E−07 |

*p > 0.05; p > 0.01; *p > 0.001.
H: Heparin control; C: Control.

The invention claimed is:

1. An in vitro method for the production of a platelet derived secretome characterized by comprising the following steps:

a) obtaining a non-activated platelet suspension free of plasma and other blood/tissue components other than platelets by the steps of:

i) centrifugation and/or filtration of a sample previously obtained from a biological source comprising platelets or from a platelet rich sample;

ii) isolation of the platelet fraction; and iii) resuspension of the platelet fraction in a buffer;

wherein step a) is performed at room temperature, and wherein step a) does not use inhibitors of platelet aggregation;

b) inducing platelet degranulation by incubating in constant shaking the non-activated platelet suspension obtained in step a) with a platelet agonist, obtaining a platelet and platelet secretome suspension;

wherein the temperature of step b) is between 35 and 40° C.; and c) collecting the platelet derived secretome by centrifug-
ing the platelet and platelet secretome suspension
obtained in step b),
wherein step c) is performed at room temperature.

2. The method of claim 1, wherein the biological source
comprising platelets, or the platelet rich sample is from a
mammal.

3. The method according to claim 1, wherein the platelet
agonist in step b) is selected from the group consisting of:
thrombin receptor activator peptide 6 (TRAP6), convulxin,
collagen, phorbol-12-myristate-13-acetate (PMA), aggretin
A, adenosine diphosphate (ADP), epinephrinerachidonic
acid and thrombin.

4. The method of claim 1, wherein the agonist in step b)
is selected from: TRAP6 at a concentration of 100 µM,
convulxin at a concentration of 0.625 ng/ml, PMA at a
concentration of 100 ng/ml, aggretin A at a concentration of
6.53 nM, collagen at a concentration of 30 µg/mL and
collagen at a concentration of 90 µg/mL.

5. The method of claim 1, wherein after step c) the platelet
secretome is sterilized by filtration or nanofiltration.

6. The method of claim 1, wherein after step c) the
secretome is stored by freezing, lyophilization, freeze dry-
ing, dehydration, encapsulation or nanoencapsulation.

7. The method of claim 6, wherein after step c) the
secretoma is nanoencapsulated.

\* \* \* \* \*